(12) United States Patent
Gladman et al.

(10) Patent No.: US 11,498,981 B2
(45) Date of Patent: *Nov. 15, 2022

(54) PROCESS FOR PRODUCING LOW ENDOTOXIN CHITOSAN

(71) Applicant: Medtrade Products Limited, Crewe (GB)

(72) Inventors: June Gladman, Appleton Thorn (GB); Craig Hardy, Audlem (GB); Andrew Hoggarth, Wistaston (GB)

(73) Assignee: MEDTRADE PRODUCTS LIMITED, Crewe (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/052,016

(22) Filed: Feb. 24, 2016

(65) Prior Publication Data
US 2016/0168277 A1 Jun. 16, 2016

Related U.S. Application Data

(62) Division of application No. 14/387,331, filed as application No. PCT/GB2013/050775 on Mar. 25, 2013.

(30) Foreign Application Priority Data

Mar. 23, 2012 (GB) .................................... 1205174

(51) Int. Cl.
*C08B 37/08* (2006.01)
*A61L 26/00* (2006.01)
*C08L 5/08* (2006.01)

(52) U.S. Cl.
CPC .......... *C08B 37/003* (2013.01); *A61L 26/008* (2013.01); *A61L 26/009* (2013.01); *A61L 26/0023* (2013.01); *A61L 26/0066* (2013.01); *C08L 5/08* (2013.01); *A61L 2300/232* (2013.01); *A61L 2300/404* (2013.01); *A61L 2300/418* (2013.01); *A61L 2400/04* (2013.01)

(58) Field of Classification Search
CPC .. C08B 37/003; A61L 26/0066; A61L 26/009; A61L 26/008; A61L 26/0023; A61L 2300/404; A61L 2300/418; A61L 2400/04
USPC .......................................................... 514/55
See application file for complete search history.

(56) References Cited

U.S. PATENT DOCUMENTS

| 4,195,175 A | * | 3/1980 | Peniston | ............... C08B 37/003 536/20 |
| 2008/0248508 A1 | * | 10/2008 | Baker | ................. C08B 37/0003 435/7.92 |

FOREIGN PATENT DOCUMENTS

| EP | 0424672 A1 | 5/1991 | | |
| EP | 1859816 A1 | 11/2007 | | |
| WO | 2005034865 A2 | 4/2005 | | |
| WO | WO 2005/034865 A2 | * | 4/2005 | |
| WO | 2006134614 A1 | 12/2006 | | |
| WO | WO 2006/134614 A1 | * | 12/2006 | ............. C03B 37/08 |
| WO | 2008063503 A2 | 5/2008 | | |
| WO | WO 2008/063503 A2 | * | 5/2008 | ............. C08B 37/00 |

OTHER PUBLICATIONS

International Search Report to corresponding International Appl. No. PCT/GB2013/050775, 3 pages.

* cited by examiner

*Primary Examiner* — Ganapathy Krishnan
(74) *Attorney, Agent, or Firm* — Tarolli, Sundheim, Covell & Tummino LLP

(57) ABSTRACT

The present invention relates to a process for producing a low endotoxin alkali chitosan, and also to a process for producing low endotoxin neutral chitosan, chitosan salt and chitosan derivatives, and to the products of such processes. The process comprises contacting chitosan with an alkali solution to form a mixture and leaving the mixture for at least about 12 hours. The low endotoxin alkali chitosan may be used the manufacture of other useful chitosan based products.

10 Claims, 5 Drawing Sheets

PROCESS FOR PRODUCING LOW ENDOTOXIN CHITOSAN

RELATED APPLICATIONS

This application is a divisional application of U.S. patent application Ser. No. 14/387,331, filed Sep. 23, 2014, which is U.S. National Stage application of PCT Application No. PCT/GB2013/050775 under 35 U.S.C. 371, filed Mar. 25, 2013, which claims the benefit of GB 1205174.4, filed Mar. 23, 2012. The entirety of each of the aforementioned applications is hereby incorporated by reference for all purposes.

TECHNICAL FIELD

The present invention relates to a process for producing a low endotoxin alkali chitosan, and also to a process for producing low endotoxin neutral chitosan, chitosan salt and chitosan derivatives, and to the products of such processes.

BACKGROUND

Chitosan is particularly useful in the preparation of haemostatic materials for use in controlling bleeding.

Chitosan is a derivative of solid waste from shell fish processing and can be extracted from fungus culture. Chitosan is a water insoluble cationic polymeric material. Before using chitosan in haemostatic materials, it is often first converted into a water soluble salt. This way, the chitosan salt is soluble in blood to form a gel which stems blood flow.

Chitosan salts are ideally suited for the applications described herein as chitosan is readily broken down in the body. Chitosan is converted to glucosamine by the enzyme lysozyme and is therefore excreted from the body naturally. It is not necessary to remove chitosan from the body. Furthermore, chitosan salts exhibit mild antibacterial properties and as such their use reduces the risk of infection.

In order to utilise chitosan in the preparation of haemostatic materials that are suitable for use in controlling bleeding, it is necessary to ensure that the chitosan has a sufficiently low concentration of endotoxin.

Endotoxin is a lipopolysaccharide existing on the surface of the outer membrane of gram-negative bacteria. Endotoxins are highly toxic to mammals, particularly humans, and are notoriously difficult to remove from materials. Endotoxins may become pyrogenic when released into the bloodstream or other tissue where they are not usually found. Thus, endotoxin must be removed from pharmaceutically acceptable products.

Treatments to remove or destroy pyrogens, particularly endotoxin, are referred to as methods of 'depyrogenation'. Techniques for the depyrogenation of materials containing endotoxin include ion exchange chromatography, ultrafiltration, distillation and various chemical processes aimed at destroying endotoxin.

WO2008063503 relates to a method of removing endotoxin from chitosan including the following steps:
  a) utilizing sterile pyrogen-free equipment and materials in a sterile environment;
  b) swelling chitosan containing endotoxins for up to 24 hours;
  c) dissolving 1 kg/25 L to 1.5 kg/25 L of the chitosan in 0.01M to 4.0M of a hydroxide base;
  d) continuously stirring the resulting chitosan base solution;
  e) heating the solution between 60-100° C. for 45 minutes to 4 hours with stirring;
  f) rinsing the solution with up to 10× volume of ultra-pure endotoxin-free water;
  g) neutralizing the solution to a pH between 6.8 and 7.5;
  h) forming an ultra-pure low endotoxin chitosan slurry and transferring to a endotoxin-free closed system;
  i) removing excess water from the slurry.

This is a complicated and costly process, especially with the need for sterile equipment and the need to rinse the solution with 10× volume of endotoxin-free water.

US2006293509 relates to a method of making a water soluble chitosan having low endotoxin by:
  (a) contacting water-insoluble chitosan with a basic solution for a first period of time of greater than 1 hour;
  (b) rinsing the water-insoluble chitosan to remove residual basic solution, desirably with endotoxin-free water;
  (c) partially acetylating the water-insoluble chitosan in a reaction solution containing a phase transfer agent;
  (d) dissolving the partially acetylated water-soluble chitosan in an aqueous solution containing a surfactant and having a pH of from about 7.0 at about 7.4;
  (e) adding a water-miscible solvent into the aqueous solution and further adjusting the pH of the aqueous solution to a pH of at least 8.0 to cause precipitation of water-soluble, chitosan having low endotoxin content from the aqueous solution/water-miscible solvent mixture; and
  (1) optionally washing in a non-solvent such as isopropanol.

However, this process is complicated and expensive and desirably involves using large quantities of endotoxin-free water or other liquids. The process also requires the use of phase transfer agents and takes place over a few hours.

TW593342 relates to a method of reducing endotoxin in chitosan by:
  (a) dissolving chitosan containing endotoxin in an aqueous solution;
  (b) contacting the aqueous solution with a surfactant to form an insoluble solid and an aqueous solution reduced in the content of the endotoxin;
  (c) using a solid/liquid separation means to separate the solid from the aqueous solution.

However, this process requires a surfactant to react with the dissolved chitosan to make an insoluble solid. The resulting solid will be a mixture of chitosan and surfactant or a reaction product between the chitosan and surfactant.

The present invention aims to alleviate the aforementioned difficulties.

SUMMARY

According to a first aspect of the present invention, there is provided a process for producing a low endotoxin alkali chitosan, the process comprising the steps of:
  (a) contacting chitosan with an alkali solution to form a mixture; and
  (b) leaving the mixture for at least about 12 hours.

According to a further aspect of the present invention, there is provided a process for producing a low endotoxin alkali chitosan, the process comprising the steps of:
  (a) contacting chitosan with an alkali solution to form a mixture;
  (b) leaving the mixture for at least about 12 hours; and
  (c) drying the mixture.

The process of the present invention provides an effective way of obtaining an alkali chitosan having a low endotoxin concentration. Advantageously, the process does not require a washing step, a rinsing step, use of a surfactant or phase transfer agents, sterile equipment and/or the use of endotoxin free water. Further, specialist air filtration or sterile conditions are also not required. The process of the present invention preferably does not comprise a step of acetylating the chitosan.

The term 'alkali solution' is used herein to refer to a solution having a pH value of greater than pH 7.5.

Since the molecular weight of endotoxins can vary significantly, endotoxin concentration is measured in endotoxin units (EU) per gram of material. The measurement of endotoxin concentration is a quantification of endotoxin levels relative to a specific quantity of reference endotoxin.

For example, in the present invention, the concentration of endotoxin is measured in endotoxin units (EU) per gram of chitosan. The term 'low endotoxin' is used herein to refer to an endotoxin concentration of less than 100 endotoxin units (EU) per gram of chitosan.

The process of the present invention is thus suitable for making an alkali chitosan that has an endotoxin concentration of less than 100 EU/g.

Preferably, the resulting alkali chitosan has an endotoxin concentration of less than 50 EU/g, more preferably less than 20 EU/g, even more preferably less than 15 EU/g and most preferably less than 10 EU/g.

It has been found that low concentrations of alkali solution are preferable in the present process. The concentration of alkali solution used in the process may be from around 0.01M to around 1M. Preferably, the concentration of alkali solution is less than 1M. Preferably, the concentration of alkali solution is from around 0.02M to 0.2M and even more preferably the concentration of alkali solution is around 0.04M to 0.06M, typically 0.05M. Concentrations of alkali solution can be around 0.01M, 0.05M, 0.10M 0.15M, 0.20M, 0.25M, 0.30M, 0.35M, 0.40M, 0.45M, 0.50M, 0.55M, 0.60M, 0.65M, 0.70M, 0.75M, 0.80M, 0.85M 0.90M or 0.95M. Good results have been observed with a concentration of 0.1M alkali solution.

In some embodiments, the quantity of alkali solution to chitosan may be in the range of from about 1 part chitosan to about 10 parts alkali solution up to about 10 chitosan to about 1 part alkali solution. Preferably, the quantity of alkali solution to chitosan is about 1 part alkali solution to about 2, parts chitosan, more preferably about 1 part alkali solution to about 1 part chitosan.

The alkali solution may comprise an alkali or alkaline earth component selected from the following, either alone or in combination: metal hydroxides, metal carbonates, metal bisulphites, metal persilicates, conjugate bases and ammonium hydroxide.

Suitable metals include sodium, potassium, calcium, or magnesium.

Preferably, the alkali component is sodium hydroxide, potassium hydroxide or sodium carbonate. Typically, sodium hydroxide is used.

The alkali solution may be contacted with the chitosan by any suitable means known in the ail. For example, the alkali solution may be sprayed onto the chitosan or the chitosan may be mixed with the alkali solution. Preferably, there is an even distribution of alkali contacted chitosan.

Preferably, the chitosan is mixed with the alkali solution. At low molecular weights, the chitosan may completely or partially dissolve in the alkali solution. The chitosan may be mixed with the alkali solution for up to around 30 minutes, more preferably for around 10 minutes. In some embodiments, the chitosan may be mixed with the alkali solution for greater than 30 minutes. In some embodiments, the mixture of chitosan and alkali solution may be stirred intermittently for the duration of step (b).

The mixture of chitosan and alkali solution is left for a period of time in which the endotoxin is destroyed by the alkali. The mixture of chitosan and alkali solution is left for at least about 12 hours. It has been discovered that the longer the period of time for which the mixture of chitosan and alkali solution is left, the lower the endotoxin concentration of the resulting alkali chitosan. Suitably low concentrations of endotoxin have been observed when the mixture has been left for around 12 hours. It is a further advantage of the process of the present invention that the mixture can be left without the need for continued mixing of the chitosan with the alkali solution.

In some embodiments, the mixture may be left for a period of at least about 13, 14, 15, 16, 17, 18, 19, 20, 21, 22, 23, 24, 25, 26, 27, 28, 29, 30, 31, 32, 33, 34, 35, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72 hours.

Preferably, the mixture is left for at least 48 hours.

In some embodiments, the mixture may be left for a period of at least about 1, 3, 4, 5, 6, 7, 8, 9, 10, 11, 12, 13, 14, 15, 16, 17, 18, 19, 20, 21, 22, 23, 24, 25, 26, 28, 29, 30, 31, 32, 33, 34, 35, 36, 37, 38, 39, 40, 41, 42, 43, 44, 45, 46, 47, 48, 49, 51, 52, 53, 54, 55, 56, 57, 58, 59, 60, 61, 62, 63, 64, 65, 66, 67, 68, 69, 70 days or more.

In some embodiments, the mixture is left for around two to four weeks (or 14 to 30 days) or more. Preferably, the mixture is left between 24 hours and 70 days, more preferably between 7 days and 35 days and most preferably between 14 days and 21 days.

Good results have been observed by contacting the chitosan with a 0.1M solution of sodium hydroxide and leaving the mixture for around 12 to 16 days, preferably around 14 days.

The mixture may be left at room temperature and pressure. By room temperature and pressure, it is meant a temperature of around 20-25° C. and a pressure of about 1 atmosphere (atm). Beneficially, the mixture does not need to be left in a sterile environment.

The mixture is preferably stored in a clean container. The mixture may be stored under an inert atmosphere.

The mixture may further comprise a preservative. Beneficially, the preservative may eliminate the risk of microbial growth that may develop, for example, when the mixture is left for a prolonged period. The preservative may be any preservative that is biocompatible and suitable for use in an alkali environment. Suitable preservatives include silver ions, zinc ions, chlorohexadine, or combinations thereof.

The process of the present invention may or may not comprise a drying step. The drying step may be performed by any conventional drying means known in the art. Preferably, the drying step is performed in an oven or by filtration through an air dryer. Again, specialist sterile equipment is not required for the drying step.

It has been discovered that, once the mixture has beer, dried in the drying step, the endotoxin level of the mixture does not noticeably increase. This is beneficial for the further processing of the mixture.

There is thus provided a low endotoxin alkali chitosan having an endotoxin concentration of less than 100 EU/g. The low endotoxin alkali chitosan may be water insoluble.

At low molecular weights, the low endotoxin alkali chitosan may show some water solubility.

According to a further aspect of the present invention, there is provided a low endotoxin alkali chitosan obtainable by the process as described herein.

According to a further aspect of the present invention, there is provided an alkali chitosan comprising an endotoxin concentration of less than 100 EU/g.

The alkali chitosan preferably has an endotoxin concentration of less than 50 EU/g, more preferably less than 20 EU/g, even more preferably less than 15 EU/g and most preferably less than 10 EU/g.

The low endotoxin alkali chitosan may be used in the manufacture of other chitosan products, such as for example, derivatives or copolymers or in the manufacture of low molecular weight chitosan or chitosan oligosaccharides. The low endotoxin alkali chitosan may also be useful as a raw material for the manufacture of other forms of chitosan or derivatives or copolymers, such as chitosan based fibres, fabrics, coatings, films, gels, solutions, sheets or foams.

In particular, the low endotoxin alkali chitosan may be used in the preparation of other useful chitosan products having low concentrations of endotoxin, including neutral chitosan and chitosan salts and other chitosan derivatives, for example, carboxymethyl chitosan, hydroxyethyl chitosan, acyl chitosan, alkyl chitosan, sulphonyl chitosan, phosphorylated chitosan, alkylidene chitosan, metal chelates, chitosan chloride, chitosan lactate, chitosan acetate, chitosan malate, chitosan gluconate.

Thus, according to a further aspect of the present invention there is provided a process for producing a low endotoxin neutral chitosan, chitosan salt or chitosan derivative comprising the step of contacting an alkali chitosan prepared by the process described herein with an acid.

The process can provide medically useful neutral chitosan, chitosan salt or other chitosan derivative having low concentrations of endotoxin.

The step of contacting the alkali chitosan with the acid may be performed before the drying step in the process according to the first aspect of the present invention.

The acid may be contacted with the alkali chitosan by any suitable means known in the art. For example, the acid may be sprayed onto the alkali chitosan or the alkali chitosan may be mixed with the acid.

Preferably, the alkali chitosan is mixed with the acid.

A neutral chitosan is referred to herein to mean a chitosan having a pH value of between about 6.5 and about 7.5, and preferably about 7.

Thus, in order to prepare a neutral chitosan, the alkali chitosan may be mixed with an appropriate volume and concentration of acid to form a neutral solution having a pH of between 6.5 and 7.5. The volume and/or concentration of acid required to neutralise the alkali chitosan will be dependent on the pH of the alkali chitosan.

Alternatively, in order to prepare a chitosan salt or chitosan derivative, the alkali chitosan may be mixed with a volume and concentration of acid in excess of that required to provide a neutral chitosan.

A suitable acid for use in the present invention may be selected from the following, either alone or in combination; organic acids, carboxylic acids, fatty acids, amino acids, lewis acids, monoprotic acids, diprotic acids, polyprotic acids, nucleic acids and mineral acids.

Suitable organic acids may be selected from the following, either alone or in combination: acetic acid, tartaric acid, citric acid, ascorbic acid, acetyl salicylic acid, gluconic acid and lactic acid.

Suitable fatty acids may be selected from the following, either alone or in combination: myristoleic acid, palmitoleic acid, sapienic acid, oleic acid, elaidic acid, vaccenic acid, linoleic acid, linoelaidic acid, α-Linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid.

Suitable amino acids may be selected from the following, either alone or in combination: histidine, lysine, aspartic acid, glutamic acid, glutamine, glycine, proline, taurine.

Suitable mineral acids may be selected from the following, either alone or in combination: hydrochloric acid, sulphuric acid and nitric acid. Preferably, the acid selected for the neutralisation is hydrochloric acid.

The acid may have a concentration of from about 0.001M acid up to the maximum possible concentration of acid. For example, the typical maximum concentration for sulphuric acid is around 98% sulphuric acid. The acid may have a concentration of from about 0.01M to 5M, 0.01M to 3M or 0.1M to 2M. Preferably, the acid has a concentration of about 1M. Concentrations of acid may be about 0.01M, 0.05M 0.10M, 0.15M, 0.2M, 0.25M, 0.30M, 0.35M, 0.40M, 0.45M, 0.50M, 0.55M, 0.60M, 0.65M, 0.70M, 0.75M, 0.80M, 0.85M, 0.90M, 0.95M or 1.0M.

The acid may be present as an acid liquor comprising the acid and a non-solvent. The non-solvent may be any solvent in which chitosan is insoluble. Typical non-solvents include ethyl lactate, ethyl acetate, methyl acetate, ethanol, acetone or mixtures thereof. Preferably, the non-solvent comprises ethyl acetate or ethanol. More preferably, the non-solvent comprises 80:20 ethanol in water. Beneficially, it has been observed that the reaction proceeds at a faster rate using a non-solvent comprising an 80:20 mixture of ethanol to water.

The ratio of chitosan to acid liquor may be from about 5 to 1 to about 1 to 5. Preferably, the ratio of chitosan to acid liquor is about 2 to 1.

In some embodiments, the low endotoxin alkali chitosan may be mixed with the acid for around five minutes. The reaction may then be allowed to happen as the mixture is dried.

The solution resulting from the mixture of alkali chitosan with acid may contain an acid salt. Preferably, the alkali solution and acid are selected to ensure that the acid salt formed is biocompatible. For example, the alkali solution may comprise sodium hydroxide and the acid may comprise hydrochloric acid. In such an example, the acid salt would be the biocompatible salt sodium chloride.

The acid salt is formed as a by-product of the reaction between the basic alkali chitosan and the acid.

The presence of an acid salt in the product can affect the usefulness of the resulting chitosan product. For example, chitosan gels to a lesser extent in saline solution than it does in water, and to an even lesser extent in saline solution at double concentration. Double concentrated saline solution referred to herein is contemplated as having an amount of sodium chloride of 1.8%. Consequently, it is desirable to have as low an amount of acid salt in the resulting chitosan product as possible and, ideally, a level of acid salt which makes little or substantially no difference to the effectiveness of the chitosan product.

It has surprisingly been discovered that using an alkali solution having a concentration of from around 0.01M to around 0.1M produces the desired low endotoxin concentration whilst also resulting in less acid salt by-product being produced in the subsequent process to produce a neutral chitosan, chitosan salt or chitosan derivative. Beneficially, less acid salt by-product means that the resulting chitosan product will have improved gelling in use over products containing a higher amount of acid salt. The process of the present invention can provide a chitosan product with a suitably low amount of acid salt without the need to wash or rinse the chitosan product. This also has the added advantage of not requiring the use of endotoxin-free water in a washing or rinsing step.

It has also been found that using low concentrations of alkali solution as described herein causes less of a reduction in the viscosity of the chitosan when producing a neutral chitosan, chitosan salt or chitosan derivative. By low concentrations of alkali, it is meant from around 0.01M to around 1M, preferably less than 1M, more preferably from around 0.02M to around 0.2M. In some embodiments, the alkali concentration may be 0.05M. In some embodiments, the alkali concentration may be as mentioned hereinabove. Beneficially, therefore, using low concentrations of alkali solution in the process is less damaging to the chitosan. It is therefore possible to remove endotoxin from chitosan whilst causing only minimal change in viscosity. It is desirable for the viscosity of the chitosan to reduce by less than about 25% in the process, preferably by less than about 15% and more preferably by less than about 10%.

Where the process provides a low endotoxin neutral chitosan, the product is suitable for use as a raw material in the production of other chitosan based products. One particular use is in the production of chitosan salts, whose absorbent properties make them desirable for use in haemostatic preparations for controlling bleeding. It is preferable that the chitosan salts are water soluble.

Thus, in another embodiment of the present invention, a low endotoxin chitosan salt may be prepared by contacting a low endotoxin neutral chitosan produced by the process described herein with an acid.

The acid may be any acid appropriate for providing the desired chitosan salt. For example, if chitosan acetate is desired, acetic acid may be used; if chitosan succinate is desired, succinic acid may be used, etc. Any of the acids described herein may be used in the present process for producing a low endotoxin chitosan salt.

The process for producing a low endotoxin chitosan salt or chitosan derivative may further comprise the step of drying the mixture of low endotoxin neutral chitosan and acid. The drying step may be performed by any conventional drying means known in the an. Preferably, the drying step is performed in an oven or by filtration of the product through an air dryer.

There is thus provided a low endotoxin neutral chitosan, chitosan salt or chitosan derivative having an endotoxin concentration of less than 100 EU/g.

The low endotoxin neutral chitosan may be water insoluble.

The low endotoxin chitosan salt may be water soluble.

According to a further aspect of the present invention, there is provided a low endotoxin neutral chitosan, chitosan salt or chitosan derivative obtainable by any of the processes described herein.

According to a further aspect of the present invention, there is provided a neutral chitosan, chitosan salt or chitosan derivative comprising an endotoxin concentration of less than 100 EU/g.

The neutral chitosan, chitosan salt or chitosan derivative preferably has an endotoxin concentration of less than 50 EU/g, more preferably less than 20 EU/g, even more preferably less than 15 EU/g and most preferably less than 10 EU/g.

The low endotoxin chitosan salt of the present invention is suitable for use as a haemostat for stemming blood flow.

Thus, according to a further aspect of the present invention, there is pro vided a low endotoxin chitosan salt as described herein for use as a haemostat for stemming blood flow.

The low endotoxin chitosan salt of the present invention may be incorporated into a wound dressing for superficial non-life threatening bleeding or life threatening bleeding.

Thus, according to a further aspect of the present invention, there is provided a low endotoxin chitosan salt as described herein for use in a wound dressing for superficial non-life threatening bleeding or life threatening bleeding.

The low endotoxin chitosan salt of the present invention is suitable for use in the preparation of a haemostatic wound dressing for stemming blood flow. According to a further aspect of the present invention, there is provided a haemostatic wound dressing comprising a low endotoxin chitosan salt as described herein.

According to a still further aspect of the present invention, there is provided a haemostatic material comprising a low endotoxin chitosan salt as described herein.

The haemostatic material and/or chitosan salt may be in any suitable form, such as particulate, powder, granular, flake, fibrous, gel, foam, sheet, film or liquid form.

According to a still further aspect of the present invention, there is provided a method of stemming blood flow comprising the steps of: optionally cleaning a wound area where possible; applying to said wound area a haemostatic wound dressing comprising a low endotoxin chitosan salt as described herein; and applying constant pressure to the wound area, until a gel clot forms.

Constant pressure is preferably applied to the wound area for about three minutes or more.

BRIEF DESCRIPTION OF THE DRAWINGS

Embodiments of the present invention will now be described further in the following non-limiting examples with reference to the accompanying drawing in which.

DETAILED DESCRIPTION

Endotoxin Testing

Figure 1:
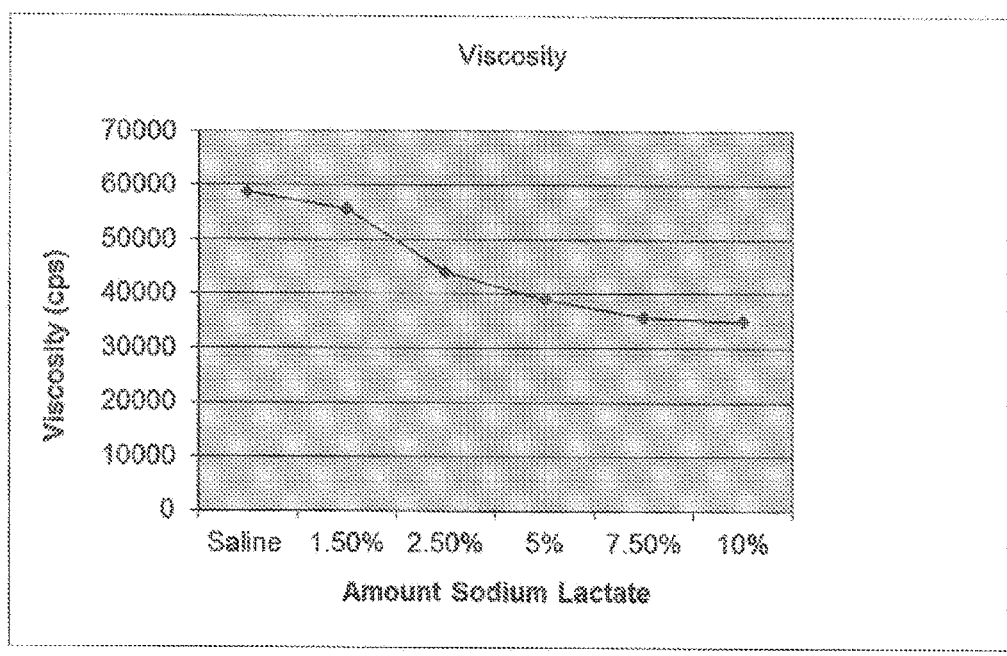
FIG. 1 is a graph displaying the effect of different concentrations of acid salt by-product on the viscosity of a chitosan product in the different media.

1. Make up USP (United States Pharmacopia) extraction solution as detailed in USP for chitosan endotoxin testing (4.6 ml of 1M HCl and 45.4 ml endotoxin free water);

2. Extract by adding 0.1 g of the test chitosan product to 9.9 ml of USP extraction solution and leave for 48 hours at 37° C.;
3. After 48 hours, dilute 100 µl of the extract in 0.9 ml of endotoxin free water; and
4. Mix 100 µl of the above in 100 µl of Endotoxin Specific (ES) buffer provided by Charles River.

The resulting extract is tested using an Endosafe®-PTS™ handheld spectrophotometer that utilises FDA-licensed disposable cartridges. The extract process uses a 2000× dilution and a minimum test limit detection of 10 EU/g.

EXAMPLES

Example 1

50 g of Chitosan (Primex Iceland) was mixed with 50 g 1M NaOH for 30 mins. The resulting wet alkali chitosan crumb was left at room temperature for 48 hours. It was then dried in an oven on a tray at 40° C.
Initial Endotoxin of raw chitosan: 383 EU/g
Dry treated alkali Chitosan: 10.6 EU/g
Control (0.1 g endotoxin free water used in extraction process instead of chitosan): <10 EU/g Example 2

50 g of Chitosan (Primex Iceland) was mixed with 50 g 0.5M NaOH for 10 The resulting wet alkali chitosan crumb was left at room temperature for 72 It was then dried in an oven on a tray at 40° C.
Initial Endotoxin of raw chitosan: 383 EU/g
Dry treated alkali Chitosan: 38.3 EU/g Example 3

50 g of Chitosan (Primex Iceland) was mixed with 50 g 0.2M NaOH for 10 The resulting wet alkali chitosan crumb was left at room temperature for seven days. It was then dried in an oven on a tray at 40° C.
Initial Endotoxin of raw chitosan: 383 EU/g
Dry treated alkali Chitosan: 27.9 EU/g Example 4

50 g of Chitosan (Primex Iceland) was mixed with 50 g 0.1M NaOH for 10 The resulting wet alkali chitosan crumb was left at room temperature for 14 It was then dried in an oven on a tray at 40° C.
Initial Endotoxin of raw chitosan: 383 EU/g
Dry treated alkali Chitosan: 12.7 EU/g Example 5

50 g of Chitosan (Primex Iceland) was mixed with 100 g 0.2M NaOH for 10 The resulting wet alkali chitosan crumb was left at room temperature for two days. It was then dried in an oven on a tray at 40° C.
Initial Endotoxin of raw chitosan: 383 EU/g
Dry treated alkali Chitosan: 35.7 EU/g Example 6

50 g of Chitosan (Primex Iceland) was mixed with 100 g 0.1M NaOH for 10 The resulting wet alkali chitosan crumb was left at room temperature for two days. It was then dried in an oven on a tray at 40° C.
Initial Endotoxin of raw chitosan: 383 EU/g
Dry treated alkali Chitosan: 49.3 EU/g Example 7

50 g of Chitosan powder (Cognis, Germany) was mixed with 50 g 0.1M NaOH for 10 mins. The resulting wet alkali chitosan crumb was left at room temperature for seven days. It was then dried in an oven on a tray at 40° C.
Initial Endotoxin of raw chitosan: 45.3 EU/g
Dry treated alkali Chitosan: <10 EU/g
Control (0.1 g endotoxin free water used in extraction process instead of chitosan): <10 EU/g Example 8

50 g of Chitosan powder (Cognis, Germany) was mixed with 50 g 0.05M NaOH for 10 mins. The resulting wet alkali chitosan crumb was left at room temperature for seven days. It was then dried in an oven on a tray at 40° C.
Initial Endotoxin of raw chitosan: 45.3 EU/g
Dry treated alkali Chitosan: <10 EU/g
Control (0.1 g endotoxin free water used in extraction process instead of chitosan): <10 EU/g Example 9

50 g of Chitosan powder (Cognis, Germany) was mixed with 50 g 0.025M NaOH for 10 mins. The resulting wet alkali chitosan crumb was left at room temperature for seven days. It was then dried in an oven on a tray at 40° C.
Initial Endotoxin of raw chitosan: 45.3 EU/g
Dry treated alkali Chitosan: <13.5 EU/g
Control (0.1 g endotoxin free water used in extraction process instead of chitosan): <10 EU/g The process can also be scaled up and used to make larger batch sizes. Examples 10 and 11 were made in a Class 100,000 cleanroom (US FED STD 209E cleanroom standards) commonly used in medical device manufacture.

Example 10

3.5 kg of Chitosan powder (Primex Iceland) was mixed with 3.5 kg 0.1M NaOH for 30 mins. The resulting wet alkali chitosan crumb was left at room temperature for 14 days. It was then dried by filtering through an air drier at 40° C.
Initial Endotoxin of raw chitosan: 288 EU/g
Dry treated alkali Chitosan: 10.2 EU/g
Control (0.1 g endotoxin free water used in extraction process instead of chitosan): <10 EU/g Example 11

3.5 kg of Chitosan (Primex Iceland) powder was mixed with 3.5 kg 1M NaOH for 30 mins. The resulting wet alkali chitosan crumb was left at room temperature for 24 hours. It was then dried by filtering through an air drier at 40° C.
Initial Endotoxin of raw chitosan: 288 EU/g
Dry treated alkali Chitosan: 15.3 EU/g
Control (0.1 g endotoxin free water used in extraction process instead of chitosan): <10 EU/g The process can be used on chitosan in different physical forms such as a chitosan fibre or chitosan fabric.

Example 12

10 g of Chitosan fibre (1.8 dtex×28 mm) was mixed with 10 g 0.1M NaOH for 10 mins. The resulting wet alkali chitosan fibre was left at room temperature for two days. It was then dried in a laboratory oven on a tray at 40° C.
Initial Endotoxin of raw chitosan fibre: 88 EU/g
Dry treated alkali Chitosan fibre: <10 EU/g
Control (0.1 g endotoxin free water used in extraction process instead of chitosan): <10 EU/g Example 13

5 g of Chitosan nonwoven fabric (60 gsm) was mixed with 5 g 0.1M NaOH for 10 mins. The resulting wet alkali chitosan fabric was left at room temperature for two days. It was then dried in a laboratory oven on a tray at 40° C.
Initial Endotoxin of raw chitosan fabric: 401 EU/g
Dry treated alkali Chitosan fabric: <78 EU/g
Control (0.1 g endotoxin free water used in extraction process instead of chitosan): <10 EU/g The following examples 14 and 15 utilise a different base to sodium hydroxide.

Example 14

50 g of Chitosan (Primex Iceland) was mixed with 50 g 0.2M KOH (potassium hydroxide) for 30 mins. The resulting wet alkali chitosan crumb was left at room temperature for seven days. It was then dried in a laboratory oven on a tray at 40° C.
Initial Endotoxin of raw chitosan: 383 EU/g
Dry treated alkali Chitosan: 14.4 EU/g
Control (0.1 g endotoxin free water used in extraction process instead of chitosan): <10 EU/g Example 15

50 g of Chitosan (Primex Iceland) was mixed with 50 g 0.5M Sodium Carbonate for 30 mins. The resulting wet alkali chitosan crumb was left at room temperature for seven days. It was then dried in a laboratory oven on a tray at 40° C.
Initial Endotoxin of raw chitosan: 383 EU/g
Dry treated alkali Chitosan: 25.8 EU/g
Control (0.1 g endotoxin free water used in extraction process instead of chitosan): <10 EU/g.

Examples 1-15 all relate to the production of low endotoxin alkali chitosan. This low endotoxin alkali chitosan can subsequently be used as a raw material to make other chitosan based products. For example alkali chitosan can be neutralised to pH 7 to form a neutral chitosan by adding a low level of an appropriate acid that would react with the base to make a biocompatible salt. For example, if sodium hydroxide is used in the basic solution, it can be neutralised by the addition of hydrochloric acid. The product would contain a low amount of residual sodium chloride.

Example 16

20 g of wet alkali chitosan crumb from Example 4 was weighed into a beaker. This contained 10 g of chitosan and 10 g of 0.1M NaOH. To neutralise the NaOH, 1 g of 1M HCl was required. This was mixed in a separate beaker with 9 g of ethanol. The acid liquid was then mixed into the wet alkali chitosan crumb and stirred for 5 The resulting mixture was then dried in a laboratory oven at 40° C. It contained 0.29% sodium chloride.

Example 17

20 g of wet alkali chitosan crumb from Example 4 weighed into a beaker. This contained 10 g of chitosan and 10 g of 0.1M NaOH. To neutralise the NaOH, 1 g of 1M acetic acid was required. This was mixed in a separate beaker with 9 g of ethanol. The acid liquid was then mixed into the wet alkali chitosan crumb and stirred for 5 minutes. The resulting mixture was then dried in a laboratory oven at 40° C. It contained 0.5% sodium acetate.

The low endotoxin alkali chitosan formed in Examples 1-15 can also be used to make a low endotoxin water soluble chitosan salt or other chitosan derivatives. Beneficially, this can be achieved without the need for a sterile environment, without the use of large quantities of expensive endotoxin free water and without the need for rinsing or washing. For example, a low endotoxin alkali chitosan can be reacted with a greater level of an appropriate acid. A small portion of the acid will react with the base to make a biocompatible salt.

Example 18

3.1 kg of dried low endotoxin alkali chitosan from Example 10 was weighed into a stainless steel mixer in a Class 100,000 cleanroom. 3.6 kg of lactic acid was premixed with 0.9 kg of endotoxin free water. This was sprayed on to the chitosan while the mixer was running. The resulting material was dried at 40° C. by filtering through an air dryer.
The material was found to be completely water soluble.
Initial Endotoxin of raw chitosan: 288 EU/g
Dry treated alkali chitosan: 10.2 EU/g (Example 10)
Dry water soluble chitosan: 13.8 EU/g
Control (0.1 g endotoxin free water used in extraction process instead of chitosan): <10 EU/g Example 19

3.1 kg of dried low endotoxin alkali chitosan from Example 11 was weighed into a stainless steel mixer in a Class 100,000 cleanroom. 3.9 kg of lactic acid was premixed with 0.9 kg of endotoxin free water. This was sprayed on to the chitosan while the mixer was running. The resulting material was dried at 40° C. by filtering through an air dryer.
The material was found to be completely water soluble.
Initial Endotoxin of raw chitosan: 288 EU/g
Dry treated alkali chitosan: 15.3 EU/g (Example 4)
Dry water soluble chitosan: 14.6 EU/g
Control (0.1 g endotoxin free water used in extraction process instead of chitosan): <10 EU/g In another example, low endotoxin alkali chitosan can also be used as a raw material for the manufacture of low endotoxin chitosan derivatives, such as carboxy methyl chitosan.

Example 20

20 g of wet alkali chitosan crumb from. Example 1 was weighed into a beaker. This contained 10 g of chitosan and 10 g of 1M NaOH. In a separate beaker a mixture of 5 g of sodium chloroacetate and 5 g of water and 10 g of ethanol was prepared. The mixed liquid was then stirred into wet alkali chitosan crumb. Its temperature was then raised to 60° C. for 4 hours. The resulting mixture was washed three times with 10 g of ethanol to remove any residual sodium chloroacetate before being dried in a laboratory oven at 40° C.

Effect of Acid Salt on Viscosity

Reacting the low endotoxin alkali chitosan with acid, to produce either a neutral pH chitosan or a chitosan salt, produces an acid salt by-product. The presence of this by-product can affect the performance of the chitosan product. For example, the level of by-product can affect the viscosity of a chitosan product in saline.

Referring to FIG. 1, there is shown the results of adding sodium lactate to saline in different concentrations, and the resulting effect of this on the viscosity of a 2 g sample of the current market-available chitosan product, CELOX®, in a 20 g solution of the different media after three minutes.

The base media was saline from body fluids, to which different levels of sodium lactate were added. The sodium lactate represented the by-product of the reaction between sodium hydroxide and lactic acid.

The results are set out in Table 1 and FIG. 1.

TABLE 1

| Concentration | Viscosity | | | |
|---|---|---|---|---|
| | Test 1 | Test 2 | Test 3 | Average |
| Saline | 55000 | 62000 | 59000 | 58667 |
| 1.5% | 54000 | 52000 | 61000 | 55667 |
| 2.5% | 50000 | 43000 | 39000 | 44000 |
| 5.0% | 35000 | 51000 | 31000 | 39000 |
| 7.5% | 35000 | 34000 | 38000 | 35667 |
| 10.0% | 37000 | 32000 | 36000 | 35000 |

It is clear from FIG. 1 that as the added salt level increases, the viscosity of the CELOX® in the media drops. It is therefore beneficial for there to be only a low level of residual salt by-product resulting in the chitosan products of the present invention.

Effect of Low Concentration Alkali Solution on Viscosity

The low endotoxin alkali chitosan produced in Example 10 was tested to demonstrate the effect of the treatment with acid on the viscosity of the chitosan polymer, considered to be a measure of molecular weight. The test followed the following method steps:

a) weigh out 5 g of low endotoxin alkali chitosan granules produced in Example 10;
b) weigh out 4.95 g of acetic acid in 600 ml beaker;
c) add 490.05 g deionised water to the beaker to make up 495 g of a 1% solution of acetic acid;
d) place the beaker on stirrer plate and turn on stir (increase as the viscosity of the solution increases;
e) add the chitosan granules to the acetic acid solution;
f) check the solution regularly until all the granules have dissolved and increase stirring level as the viscosity of the solution increases, if required;
g) leave the solution for a total of 24 hours, measured from the time the chitosan granules were introduced into the acetic acid solution;
h) attach a spindle 64 to a Brookfield Viscometer
i) set the spindle to 10 rpm;
j) insert the spindle into the solution to the mark on the spindle and turn the viscometer on and allow to stabilise;
k) record the viscosity (cPs) at selected time intervals.

The results of the above described viscosity test are shown in Table 2 below and FIG. 2. For each Batch, an average was taken over three readings at each time interval.

TABLE 2

| | Viscosity (cPs) | | | | | |
|---|---|---|---|---|---|---|
| | Batch 1 (washed) | | Batch 2 (washed) | | Batch 3 (washed) | |
| Weeks | Average | STD | Average | STD | Average | STD |
| 0 | 419.9 | 0.0 | 399.9 | 34.6 | 419.9 | 34.6 |
| 1 | 379.9 | 34.6 | 379.9 | 34.6 | 419.9 | 0.0 |
| 2 | 399.9 | 34.6 | 419.9 | 0.0 | 359.9 | 0.0 |
| 4 | 239.9 | 0.0 | 239.9 | 0.0 | 239.9 | 0.0 |
| 8 | 180.0 | 0.0 | 180.0 | 0.0 | 219.9 | 34.6 |
| 12 | 166.7 | 5.8 | 110.0 | 0.0 | 170.0 | 0.0 |
| 16 | 110.0 | 0.0 | 96.7 | 5.8 | 123.3 | 5.8 |
| 24 | 120.0 | 0.0 | 100.0 | 34.6 | 190.0 | 34.6 |

Figure 2:
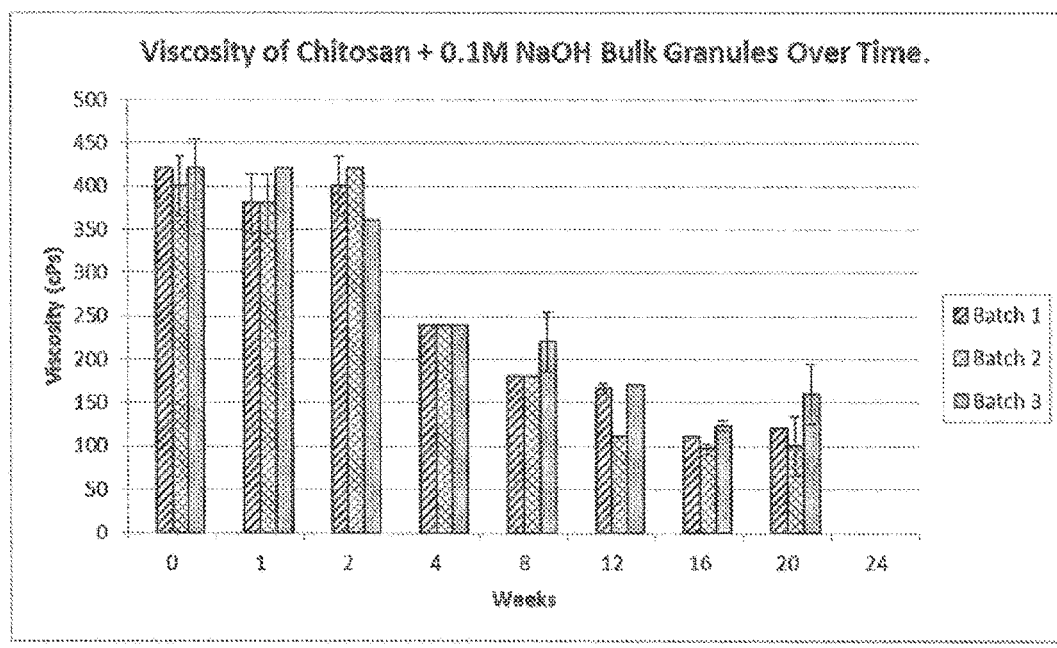
FIG. 2 is a graph showing the effect of the treatment with acid on the viscosity of the chitosan polymer.

It can be deduced from the viscosity measurements shown in FIG. 2 that the molecular weight of the low endotoxin alkali chitosan polymer prepared using a 0.1M sodium hydroxide solution is stable for weeks.

Effect of Lowering the Concentration Alkali Solution

The effect of using a lower concentration of alkali solution in the process of the present invention was tested in three experiments, focussing on (1) the percentage penetrability of saline into the test samples, (2) the time period to blood clotting and (3) the percentage haemostasis in epigastric sever in-vivo models.

Figure 3:
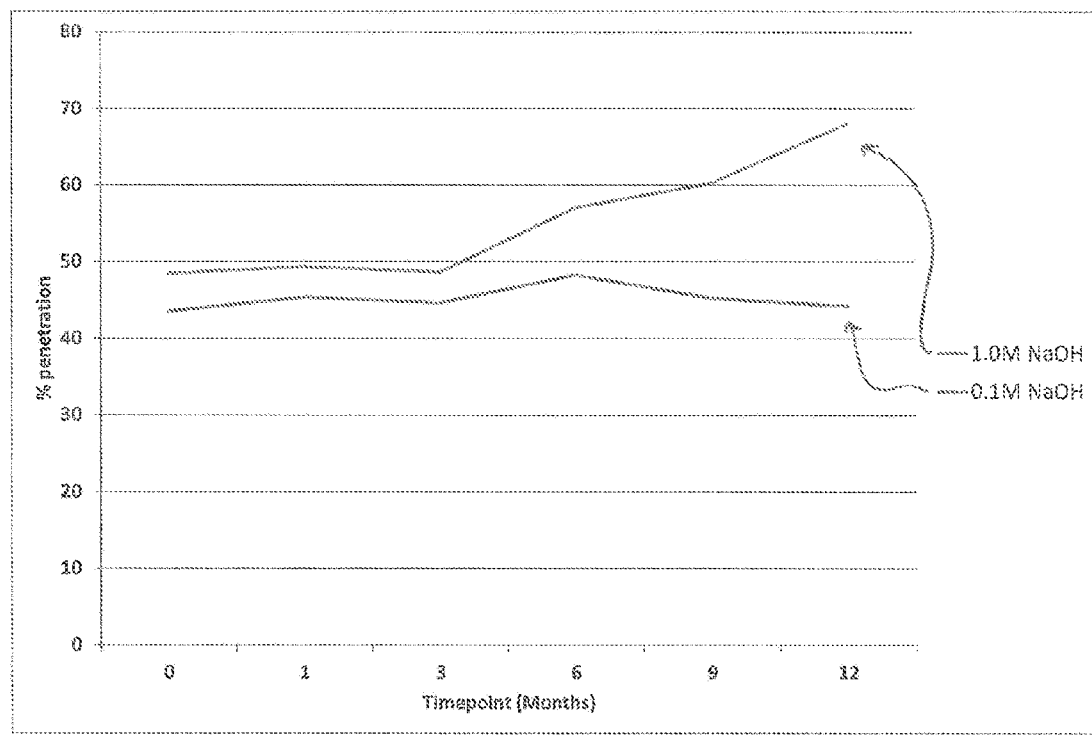
FIG. 3 is a graph showing the penetration of saline into two different haemostatic materials according to the present invention.

Referring to FIG. 3, there is shown the results of the penetrability testing.

The general test method was as follows: 5 mls of distilled water was added to a test tube. A drop of red food dye was added to the water. 3 g of sample haemostatic powder was gently tipped on top of the water such that a layer was formed. After 1 the di stance traveled by the water into the haemostatic powder was measured and recorded as percentage penetration.

As can be seen in FIG. 3, the haemostatic powder prepared by using 1.0M sodium hydroxide is less stable over time compared to the haemostatic powder prepared using 0.1M sodium hydroxide and the increasing penetration into the granules by the saline solution indicates a greater opportunity for blood to pass through the granules and not form the gel plug.

Figure 4:
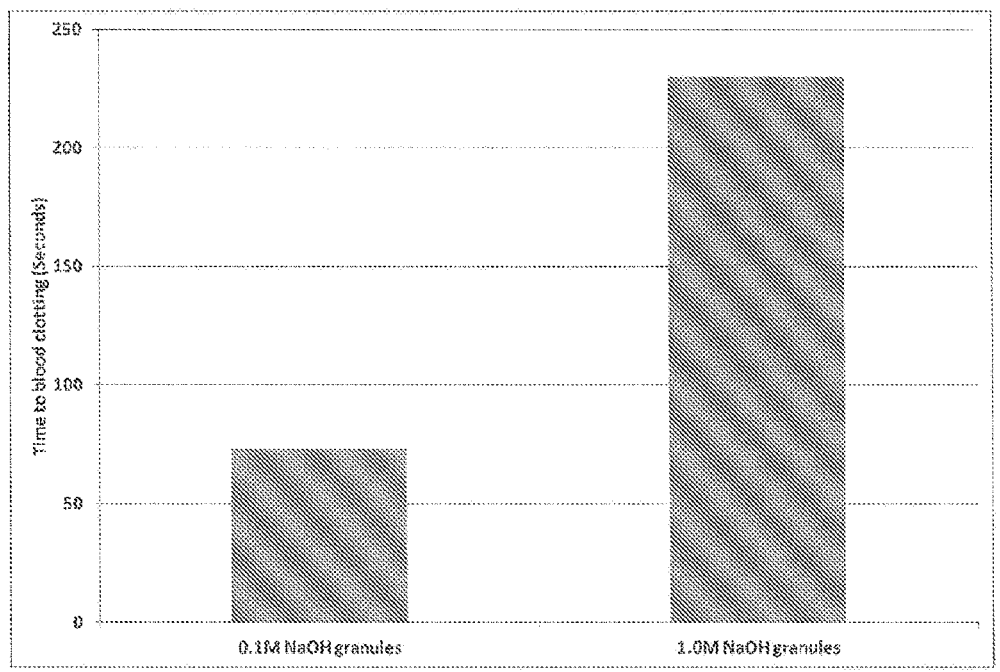
FIG. 4 is a graph showing the time period for blood clotting of two different haemostatic materials according to the present invention.

Referring to FIG. 4, there is shown the results of the blood clotting testing.

The general test method was as follows: 0.75 g of sample haemostatic powder was added to a test tube, to which 5 ml of heparinised rabbit blood was added. The test tube was then inverted and the time taken to fully clot the blood into a gel mass recorded.

As can be seen in FIG. 4, the haemostatic powder prepared by using 1.0M sodium hydroxide takes longer to clot the blood than the haemostatic powder prepared by using 0.1M sodium hydroxide. The time period is approximately three times longer, which relates to lower haemostatic properties (data has shown that time periods greater than 180 seconds does not result in 100% haemostasis in a low pressure, medium volume in-vivo bleed model.

Figure 5:
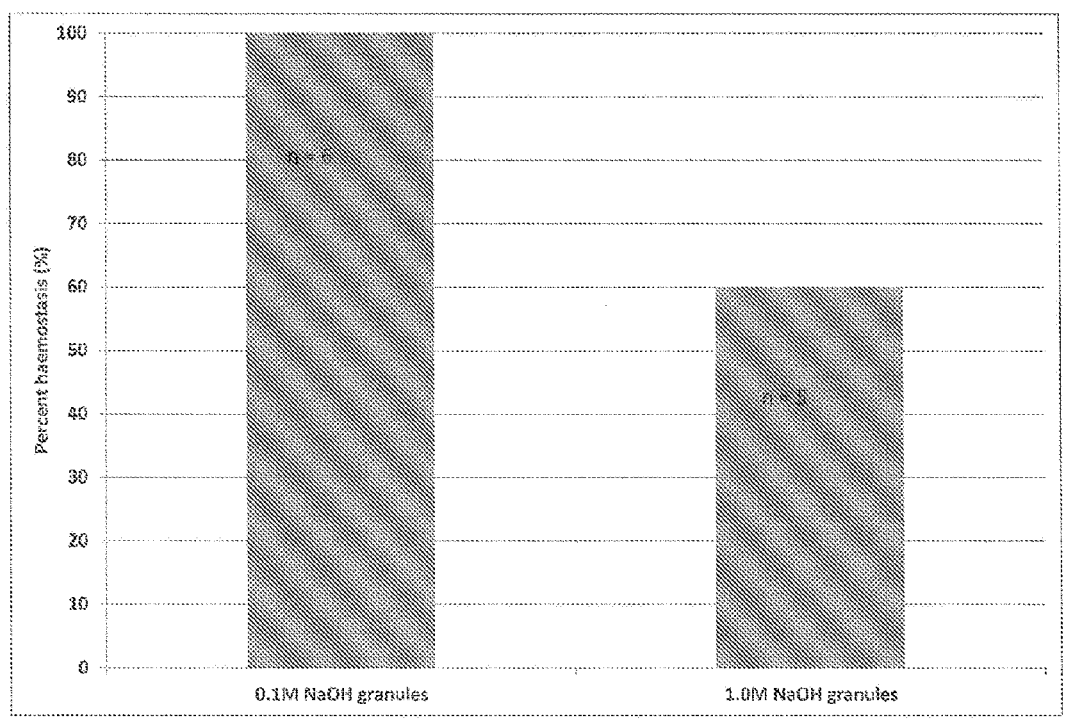
FIG. 5 is a graph showing the percentage haemostasis in epigastric sever tests of two different haemostatic materials according to the present invention.

Referring to FIG. 5, there is shown the results of the haemostasis testing.

The general test method was as follows: a 3-5 cm sever was made in the epigastric artery of a swine model (non-heparinised). The haemostatic material in granular form was applied and a 1 minute compression applied. If re-bleeding occurred a further 1 minute compression was undertaken.

As can be seen in FIG. 5, the haemostatic granules prepared by using 1.0M sodium hydroxide obtained haemostasis in 60% of the tests, compared to 100% with the haemostatic granules prepared by using 0.1M sodium hydroxide.

The test results indicate that lower the concentration of alkali solution used in the preparation of the haemostatic material of the present invention, the better the material performs in penetrability, blood clotting and haemostasis.

It is of course to be understood that the present invention is not intended to be restricted to the foregoing examples which are described by way of example only.

The invention claimed is:

1. A low endotoxin alkali chitosan, having an endotoxin concentration of less than 50 EU/g, produced by a process comprising the steps of:
    (a) contacting chitosan with an alkali solution having a concentration of from 0.01M to 0.2M to form a mixture; and
    (b) leaving the mixture for at least 12 hours.

2. A low endotoxin neutral chitosan produced by a process comprising the step of contacting the alkali chitosan of claim 1 with an acid.

3. A low endotoxin chitosan salt produced by a process comprising the step of contacting the alkali chitosan of claim 1 with an acid.

4. A low endotoxin chitosan derivative produced by a process comprising the step of contacting the alkali chitosan of claim 1 with an acid;
    wherein the chitosan derivative is selected from the group consisting of carboxymethyl chitosan, hydroxyethyl chitosan, acyl chitosan, alkyl chitosan, sulphonyl chitosan, phosphorylated chitosan, alkylidene chitosan, metal chelates, chitosan chloride, chitosan lactate, chitosan acetate, chitosan malate and chitosan gluconate.

5. A haemostatic wound dressing comprising the low endotoxin chitosan salt of claim 3.

6. A method for using a low endotoxin chitosan salt as a haemostat for stemming blood flow, or as a wound dressing for superficial non-life threatening bleeding or life threatening bleeding, the method comprising the steps of:
    applying to said wound area a haemostatic wound dressing comprising the low endotoxin chitosan salt of claim 3; and
    applying constant pressure to said wound area until a gel clot forms.

7. The low endotoxin alkali chitosan of claim 1, wherein the quantity of alkali solution to chitosan is in the range of from 1 part chitosan to 10 parts alkali solution to 10 parts chitosan to 1 part alkali solution.

8. A low endotoxin neutral chitosan produced by a process comprising the step of contacting the alkali chitosan of claim 1 with an acid;
    wherein the acid is selected from the group consisting of organic acids and mineral acids.

9. The low endotoxin alkali chitosan of claim 8, wherein the acid is selected from the group consisting of carboxylic acids, fatty acids, lewis acids, monoprotic acids, diprotic acids, polyprotic acids, and nucleic acids.

10. The method of claim 6, further comprising cleaning a wound area where possible prior to applying to said wound area a haemostatic wound dressing.

* * * * *